US00PP19147P2

(12) United States Plant Patent
Messenbrink et al.

(10) Patent No.: US PP19,147 P2
(45) Date of Patent: Aug. 26, 2008

(54) ***COREOPSIS* PLANT NAMED 'LIGHTNING FLASH'**

(50) Latin Name: *Coreopsis triperis*
Varietal Denomination: Lightning Flash

(76) Inventors: Mark Messenbrink, 6262 NC 58 North, Nashville, NC (US) 27856; Louisa Messenbrink, 6262 NC 58 North, Nashville, NC (US) 27856

( * ) Notice: Subject to any disclaimer, the term of this patent is extended or adjusted under 35 U.S.C. 154(b) by 17 days.

(21) Appl. No.: 11/709,537

(22) Filed: Feb. 21, 2007

(51) Int. Cl.
*A01H 5/00* (2006.01)

(52) U.S. Cl. ..... Plt./417

(58) Field of Classification Search ..... Plt./417

See application file for complete search history.

*Primary Examiner*—Kent L Bell

(74) *Attorney, Agent, or Firm*—Klarquist Sparkman, LLP

(57) ABSTRACT

A new and distinct *Coreopsis* plant named 'Lightning Flash' characterized by the bright golden yellow foliage in the spring and on youngest foliage throughout the season, a tall, upright habit, bright golden daisy like inflorescences with dark centers, late summer and fall flowering season, and excellent vigor.

1 Drawing Sheet

Botanical designation: *Coreopsis tripteris*.
Variety denomination: 'Lightning Flash'.

BACKGROUND OF THE INVENTION

The present invention relates to a new and distinct plant of *Coreopsis* and given the cultivar name 'Lightning Flash'. *Coreopsis* is in the family Asteraceae. The new cultivar originated as a chance seedling in a bed of *Coreopsis tripteris* seedlings at the nursery in North Carolina.

SUMMARY OF THE INVENTION

The following traits have been repeatedly observed and are determined to be the unique characteristics of 'Lightning Flash'. These characteristics in combination distinguish 'Lightning Flash' as a new and distinct cultivar:

1. Bright golden yellow foliage in the spring and on youngest foliage throughout the season
2. Tall, upright habit
3. Bright golden daisy like inflorescences with dark centers
4. Late summer and fall flowering season
5. Excellent vigor.

This new cultivar has been reproduced only by asexual propagation (division and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPHS

FIG. 1 shows a two year old *Coreopsis* 'Lightning Flash' growing in the ground in the trial field in full sun in August in Canby, Oreg.

FIG. 2 shows a close up of the flowers.

DETAILED PLANT DESCRIPTION

The following is a detailed description of the new *Coreopsis* cultivar based on observations of a two-year-old specimen grown in the ground in full sun under typical outdoor conditions in the trial fields in September in Canby, Oreg. Canby is zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zone 4.
- *Size.*—50 cm wide and 90 cm tall to top of inflorescences.
- *Form.*—Clumping.
- *Vigor.*—Excellent.
- *Roots.*—Fibrous, thickened, Yellow White 158A; roots develop easily from crown divisions.

Stem:
- *Type.*—Ascending.
- *Size.*—80 cm tall and 7 mm wide.
- *Internode length.*—15 to 54 mm.
- *Surface.*—Glabrous.
- *Color.*—Yellow Green 148D to 148C at the base.

Leaf:
- *Type.*—Compound, tripartite, some basal leaves with the middle leaflet 3-parted.
- *Shape.*—Ovate overall, lobes narrowly oblong lanceolate, terminal lobe is the longest, grows to 9 cm long and 9 mm wide, side lobes grow to 6.6 cm long.
- *Arrangement.*—Opposite.
- *Blade size.*—Grows to 10 cm long and 8 cm wide.
- *Margins.*—Entire.
- *Apex.*—Acute.
- *Base.*—Attenuate.

*Petiole description.*—Grows to 4 cm long, 1.5 mm wide, clasping, glabrous, Yellow Green 147B.

*Surface texture.*—Glabrous on both sides.

*Venation.*—Pinnate.

*Color.*—Spring and early summer — Top side Yellow 3B on both sides with older leaves darkening to a combination of Yellow Green 153C and Green 146B (bottom closest to Yellow Green 146D) summer — Yellow Green 153C with lower leaves Yellow Green 147B with bottom sides the same.

Immature inflorescence: Globular, 6 mm wide and 8 mm deep, glabrous, Greyed Green 197A with Yellow Green 151C on tip.

Inflorescence:

*Type.*—Sub-corymbose, with 3 to 9 capitula per branch and 13 branches per stem.

*Peduncle.*—Grows to 5.5 cm long and 0.8 mm wide, glabrous, Yellow Green 146B.

*Capitula size.*—4.5 cm wide and 1.3 cm deep.

*Ray florets.*—8 in number, no pistil or stamen, broadly elliptic, the tip three notched, acute, margins entire, base obtuse, grows to 23 mm long and 9 mm wide, glabrous and Yellow 12A on both surfaces, 1 mm claw at base.

*Cone.*—Flat topped, grows to 11 mm wide and 4 mm deep, Greyed Purple 187A.

*Disc florets.*—Corolla — 4 mm long and 1.5 mm wide, tubular, 4 lobed, Greyed Purple 187B closest to lobes and on main veins to Yellow White 158A on tube inside and out, glabrous Pistil — 9 mm long, 2-branched stigma 1 mm long extruding from the corolla, Greyed Purple 187A, style 4 mm long, Green Yellow 1C, ovary 3 mm long, Green Yellow 1C Stamen — 4, filaments 3 mm long, extruding, Black 202A, pollen Yellow 12C.

*Pyllaries.*—In 2 alternating series, each with 8 lobes, series closet to ray florets, ovate, entire, acute, 7 mm long and 3 mm wide, overlapping, glabrous, Greyed Green 197A; lower series with lobes liner, 4 mm long and 1 mm wide at the base, entire, acute, glabrous, Yellow Green 46B.

*Bloom period.*—Late August through September in Canby, Oreg.

*Fragrance.*—None.

Seed: None observed as there was no other plant to outcross with

*Fertility.*—Fertile.

Disease and pests: *Coreopsis* are susceptible to mildew and fungal spots. No known resistances on the new cultivar.

COMPARISONS TO SIMILAR *COREOPSIS*

Compared to *Coreopsis tripteris,* the new cultivar differs in its unique gold foliage color.

I claim:

1. A new and distinct *Coreopsis* plant as herein illustrated and described.

* * * * *

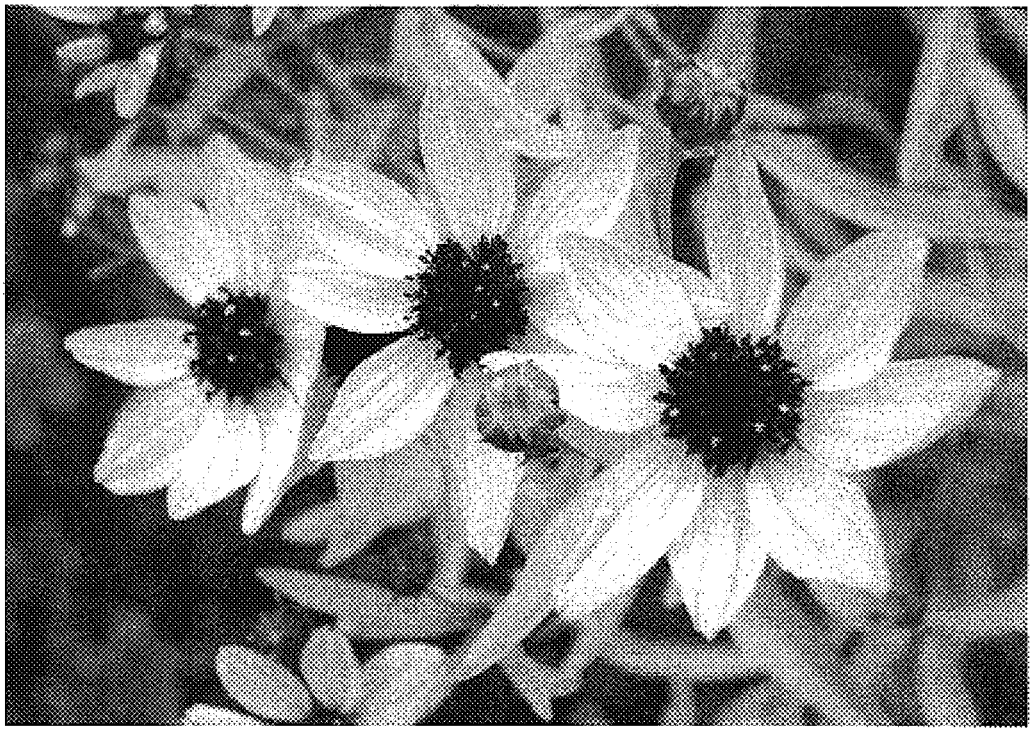

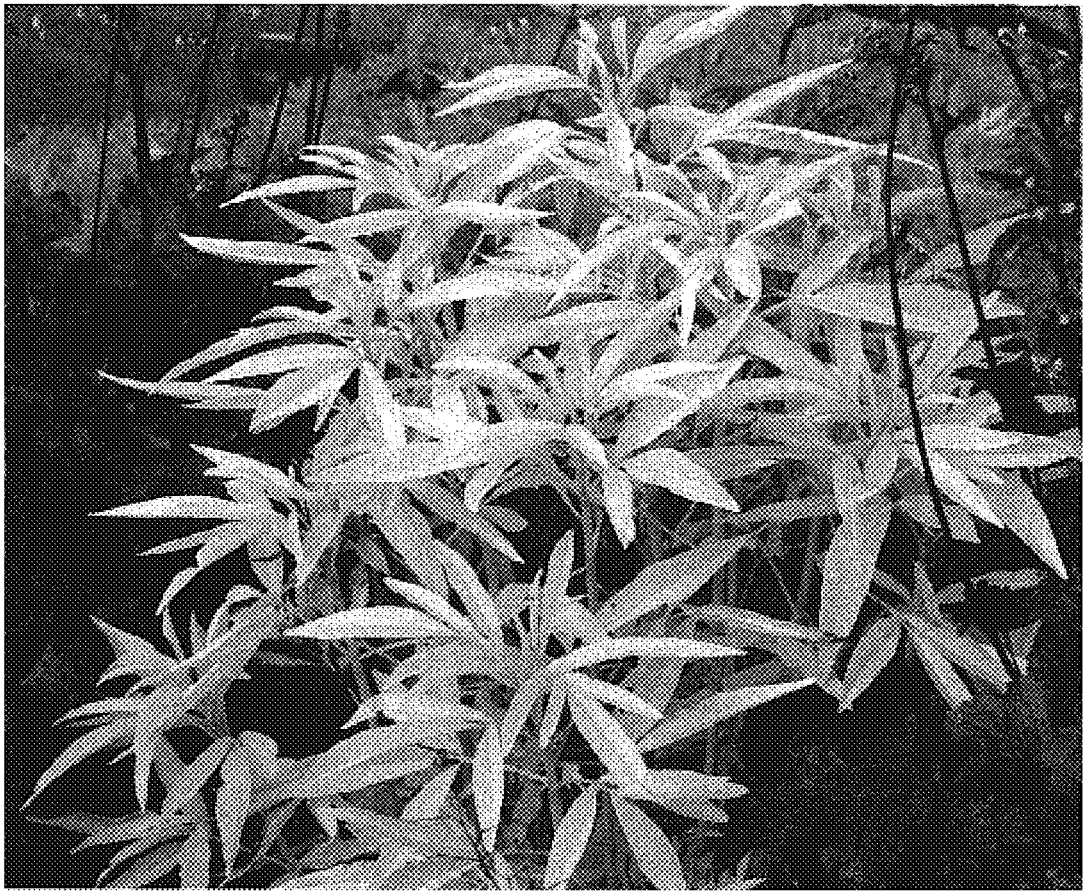
Figure 1 above, Figure 2 below.